United States Patent [19]
Matuszewski et al.

[11] Patent Number: 6,139,486
[45] Date of Patent: Oct. 31, 2000

[54] METHOD AND DEVICE FOR BIOMAGNETIC ENHANCED COLD THERAPY

[76] Inventors: Robert E. Matuszewski, P.O. Box 4652, Englewood, Colo. 80155; Robert Senter, 343 Morningstar Way, Castle Rock, Colo. 80104

[21] Appl. No.: 09/369,352

[22] Filed: Aug. 6, 1999

Related U.S. Application Data

[60] Provisional application No. 60/095,666, Aug. 7, 1998.

[51] Int. Cl.[7] ..................................................... A61N 1/00
[52] U.S. Cl. ................................ 600/15; 607/96; 607/114
[58] Field of Search ............................ 600/9–15; 607/96, 607/114, 108–112, 152; 602/13; 383/901; 165/46; 126/204

[56] References Cited

U.S. PATENT DOCUMENTS

| | | | |
|---|---|---|---|
| 4,517,972 | 5/1985 | Finch, Jr. | 602/2 |
| 4,592,358 | 6/1986 | Westplate | 607/112 |
| 4,886,063 | 12/1989 | Crews | 607/112 |
| 4,981,135 | 1/1991 | Hardy | 607/108 |
| 5,738,624 | 4/1998 | Zablotsky et al. | 600/9 |
| 5,951,459 | 9/1999 | Blackwell | 600/13 |

*Primary Examiner*—Cary O'Connor
*Assistant Examiner*—Catherine McPherson
*Attorney, Agent, or Firm*—Bruce L. Plotkin

[57] ABSTRACT

An apparatus for applying magnetic and cold therapy to an affected body part includes a stretch type flexible sheath capable of being secured about an injured portion of tissue, one or more packets provided in the interior of the sheath, such packets being flexible within cold temperature ranges, and one or more magnets provided in the gel packet itself, or interior or exterior of the sheath, either by insertion or sewing the magnet into the sheath. According to another embodiment of the invention, an apparatus for simultaneous applying magnetic and cold therapy to body parts features cold therapy gel packets and magnets that are separately insertable into pockets formed in a sheath for application to a body part. According to the method of the present invention, a magnetic field and cold compress are simultaneously applied to an injured body part. Additionally, the present invention discloses a gel packet for cold therapy enclosing permanent magnets for magnetic therapy.

13 Claims, 7 Drawing Sheets

METHOD AND DEVICE FOR BIOMAGNETIC ENHANCED COLD THERAPY

RELATED APPLICATIONS

This application claims the benefits under 35 U.S.C. § 119(e) from U.S. Provisional Patent Application No. 60/095,666 entitled "METHOD AND DEVICE FOR BIOMAGNETIC ENHANCED COLD THERAPY" filed Aug. 7, 1998, which is incorporated by reference herein in its entirety.

FIELD OF THE INVENTION

The present invention is directed to a method and apparatus for applying magnetic(s) and cold therapy simultaneously to body parts, and in particular, is directed to an apparatus having individual cold therapy packets and a universal apparatus containing or combining ceramic, flexible, neodymium and composition magnets such as aluminum, nickel, ferrite and cobalt and/or ferrite based composite magnets in combination with a glycol and water based gel capable of being frozen, or cooled, such apparatus useful in the treatment of bone, muscle, joint and blood disorders, including but not limited to polio, arthritis and diabetes.

BACKGROUND OF THE INVENTION

Doctors, trainers, physical therapists and professional athletes frequently recommend that their patients and athletes ice injuries or strained and fatigued body parts immediately after injury and/or strenuous activity for at least fifteen minutes, but no longer than thirty minutes, over a period of forty-eight hours. Cold is known to relieve pain and inflammation by its direct effects on circulation and metabolism. A reduction in temperature to any injured body part, whether minor or acute, causes blood vessels and blood cells in the area of trauma to shrink in size, thus slowing the flow and rush of fluids into areas of irritated tissue. This decrease in swelling and inflammation in turn reduces pain.

Magnetic field therapy is known to stimulate the circulation of blood, improve the oxygen consumption of blood cells, and reduce inflammation and fluid retention. These attributes are believed to promote healing and to reduce pain in those areas of the body where the magnetic field therapy is applied.

Heretofore, an apparatus has not been provided that combines both magnetic and cold therapy for simultaneous application to an injury. Thus, this combination of cold therapy and biomagnetic therapy combined in one universal size apparatus allows the typical icing period to be extended to more than double the recommended icing time, while simultaneously achieving the benefits of increased cellular movement, oxygenation of blood cells and circulation through magnetics. Accordingly, this combination of both ice therapy and magnetic therapy provides a more dramatic and rapid response than with either form of therapy used separately and it would be advantageous to have such an apparatus and associated method to treat various ailments.

SUMMARY OF THE INVENTION

The present invention combines biomagnetics, magnetics and magnetism, and cold therapy to reduce pain, decrease inflammation and swelling, to stop or reduce bleeding and to promote healing of injuries. By allowing both magnetic and cold therapy to be applied using one device, the present invention provides for the alleviation of pain and facilitates the healing of injured tissue.

The present invention is directed to a device and method that simultaneously provides cooling and magnetic flux to an injured area of tissue to which the device is applied. In particular, the device of the present invention includes one or more flexible packets having a gel therein. When the packets are cooled to freezing and below freezing temperatures and subsequently applied to the injured area, the packets are capable of retaining, for an effective period of time (e.g., approximately 40 to 60 minutes and longer based on the exact combination of glycol and water.), a temperature in a range that is below the temperature the injured tissue would be if untreated by cold therapy. Further, the packets in the frozen state are also flexible enough to conform to, for example, the contour of the injured area. The present invention includes one or more magnets for providing magnetic flux to the injured area. In one embodiment, the magnets have a magnetic flux density in the range of 800 to about 2500 gauss, however, magnets can be used effectively that have a magnetic flux density in a range of about 500 to about 5000 gauss.

Note that both the gel packets and the flexible and non-flexible magnets are secured within the interior of an outer flexible sheath that is, in turn, capable of being applied to the injured area. In particular, the flexible, universal fit sheath may include attachment mechanisms such as hooks, snaps, belts, buckles, and elastic or hook-and-loop material for securing the device of the present invention about the injured area. Alternatively, the device may be laid upon a user (e.g., a user's, or horse's back or shoulder) without it being bound to the user. The device may also be used to treat injuries to animals, as well as to humans. Thus, the present invention is capable of being used on, e.g., horses, camels, dogs and cats.

In one embodiment, each of the gel packets includes a ferrite based, rare earth material flexible magnet therein. This magnet within the gel packet acts as a conductor of the magnetic flux produced by the magnets, promoting the establishment of a magnetic field within the gel packet. The magnet and gel combination is believed to reduce or eliminate irritation that can result to a users skin due to magnetic strips being placed directly on, or in too close a proximity to, the user. In particular, it is believed that the magnet being placed within the gel packet distributes the magnetic flux, thereby creating a more even distribution of flux about the interior of the sheath. The magnets are arranged in one embodiment so as to provide magnetic flux over substantially the entire user contact area of the sheath. In other embodiments, each of the gel packets has a corresponding one of the magnets attached thereto and/or provided therein.

It is an aspect of the present invention that it can be applied to an injured area for an extended period of time. In particular, since the gel packets substantially reach ambient temperatures within about 60 minutes, and more preferably within about 45 minutes, the cold therapy aspect of the present invention dissipates while the magnetic flux induced by the magnets therein retains its beneficial effects of increasing oxygen and blood flow to the injured area. Thus, the invention and apparatus can be worn comfortably for an extended period of time, including but not limited to overnight and periods of 8 to 12 hours at a time.

It is also an aspect of the present invention that the device of the present invention and/or the gel packets therein can be re-cooled so that the device can be reapplied to the injured area for repeating the process of both cooling and inducing a magnetic flux at the injured area.

It is a further aspect of the present invention that the magnets may be flexible, rigid, or ceramic such as flexible magnetic strips, squares, ovals, neodymium, rare earth and aluminum, nickel and cobalt based magnetic materials. In one embodiment of the present invention, the flexible magnets each contain an alternating North and South pole pattern so that the North and South poles are positioned approximately 4 to 6 mm apart in a concentric circle pattern, thus allowing magnetic field penetration to remain perpendicular to the blood flow of the injured area(s). In another embodiment, each magnet, of flexible or non-flexible magnetic material, is also aligned parallel to each of the other magnets to maintain this constantly alternating pole pattern.

In another aspect of the invention, the gel packets and magnets are removable from the fabric covering of the apparatus. This allows for the replacement of individual gel packets and flexible and non-flexible magnets. Additionally, this allows the present invention to maintain a universal fit and one-size fits all approach to the body area to which it is to be applied. One embodiment of the invention has seven pouches to receive seven magnets and gel packets providing cold and magnetic therapy for foot, ankle, shin, knee, thigh, hand, wrist, elbow and arm. Another embodiment of the invention has five pouches to receive five magnets and gel packets providing cold and magnetic therapy for shoulder, neck, back, buttocks, hip and abdomen. Other sizes and pouch configurations may also be provided for specific areas of the body.

In yet another aspect of the invention, the apparatus allows for the insertion and/or permanent application of flexible and non-flexible magnets into the sheath and or sheath pockets of the apparatus separately from that of the individual gel packets. This separation of the magnetics and gel is an option for those users preferring the magnetic device to be placed closer to and further away from the skin or area of injury. For this aspect of the invention, both flexible and non-flexible magnets may be separately provided.

Other features and benefits of the present invention will become evident from the detailed description herein below and the accompanying drawings.

DETAILED DESCRIPTION OF PREFERRED EMBODIMENTS

Figure 7:
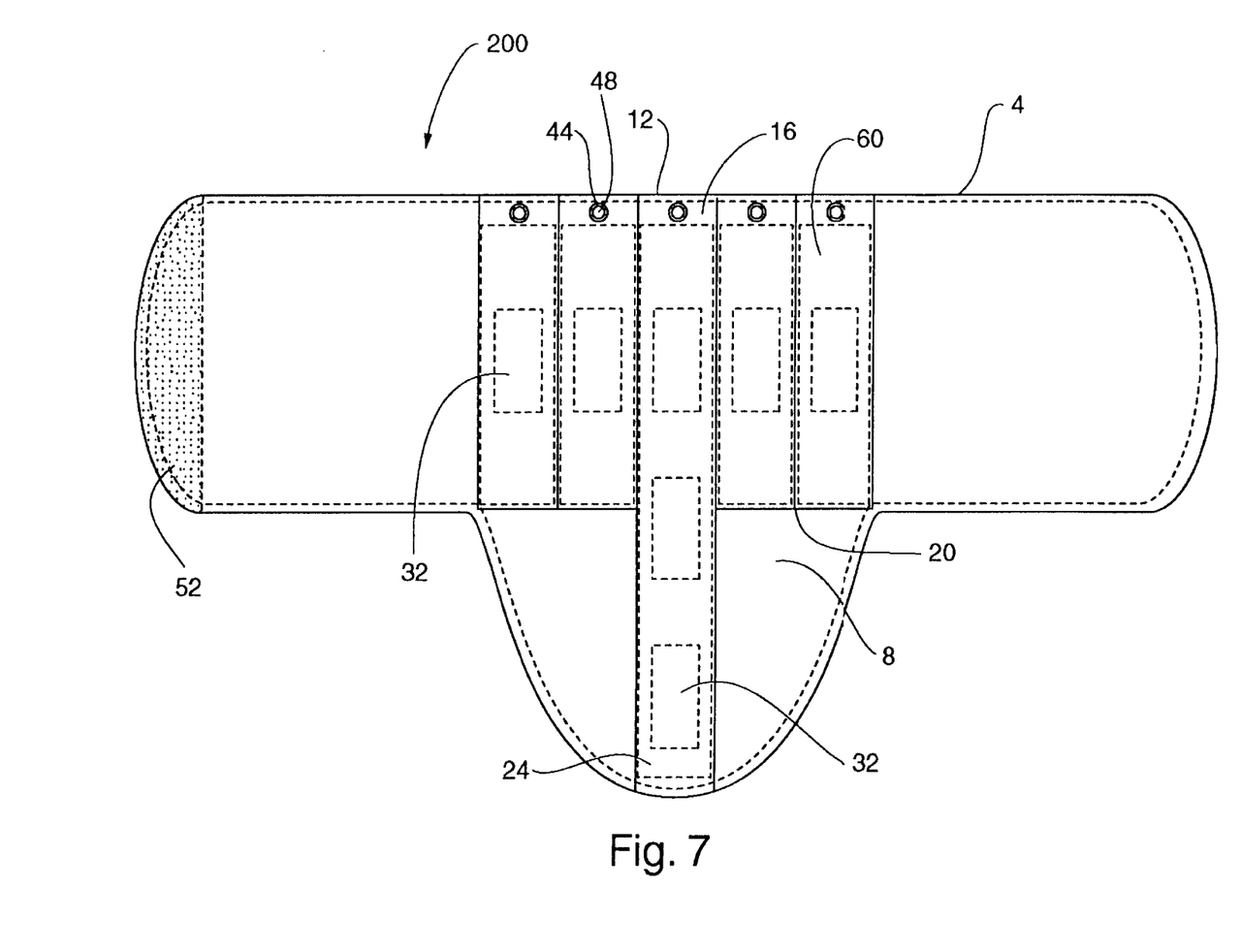
FIG. 7 is a plan view of another embodiment of the apparatus suitable for use on the upper and lower back, hip, buttocks, shoulder, neck and abdomen.

The present invention provides a non-obvious combination of magnetics and cold therapy for application to any afflicted human or animal body part. The product is available in a number of versions to accommodate a variety of sizes and human and animal body parts. In a first embodiment, illustrated in FIGS. 1 and 2, a device, constructed in accordance with the present invention is designed specifically, but not limited to use on the foot, ankle, shin, knee, thigh, leg, hand, wrist, forearm, elbow and arm, including but not limited to humans, dogs, cats and horses. A second embodiment of the present invention, illustrated in FIG. 7, is designed specifically for, but not limited to use on the upper and lower back, hip, buttocks, shoulder, neck and abdomen, including but not limited to dogs, cats and horses. Both of the illustrated embodiments of the apparatus are one size fits all designs. An increase in temperature of a refrigerated ice, or cold therapy unit, once removed from a freezer, has been previously considered a disadvantage. The advantage of the present invention is that, as recommended by physicians, trainers and professional athletes, icing should only take place in fifteen to thirty minute increments. As the gel packets surrounding the affected area increase in temperature, the cold therapy apparatus is no longer considered useful or nontherapeutic. Instead, due to the combination of biomagnetics and the gel, the magnetics continue to maintain their effect on the affected area of pain, strain or injury, thus creating an apparatus that may be worn extensively through the healing process.

Figure 1:
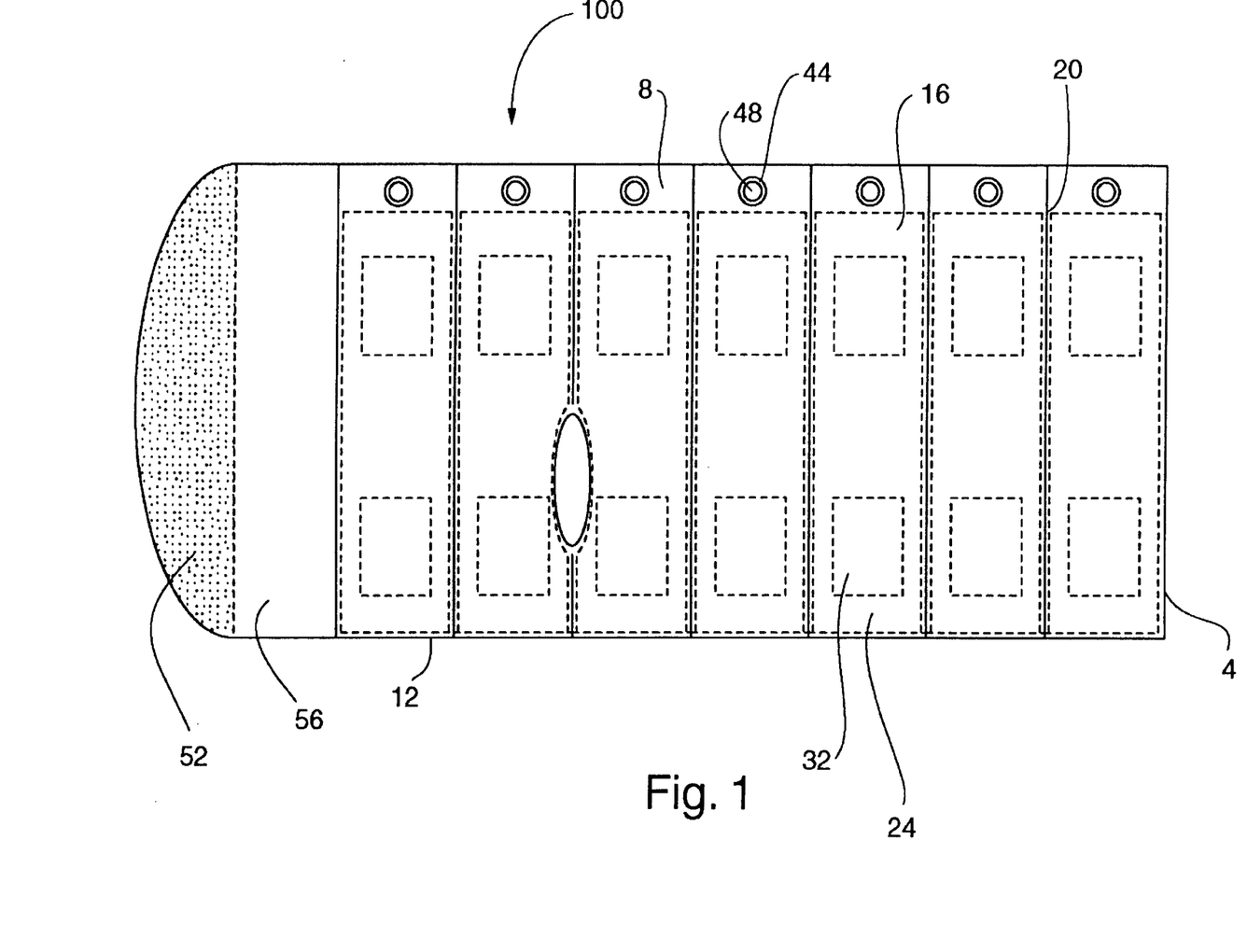
FIG. 1 is a plan view of one embodiment of the device particularly well-suited for use on the foot, ankle, shin, knee, thigh, hand, wrist, forearm, elbow and arm.
Figure 2:
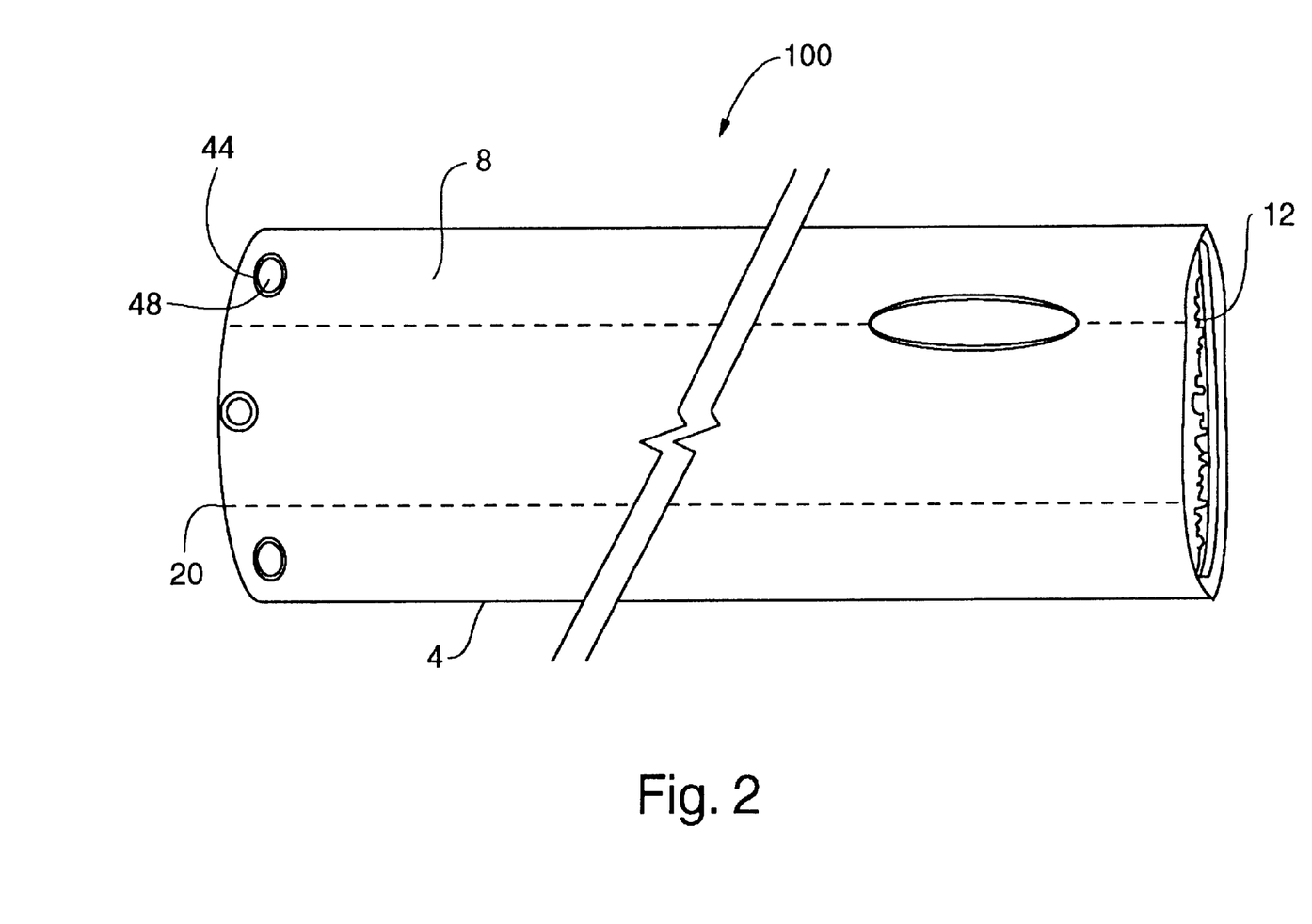
FIG. 2 is a perspective view of the embodiment of FIG. 1.
Figure 3:
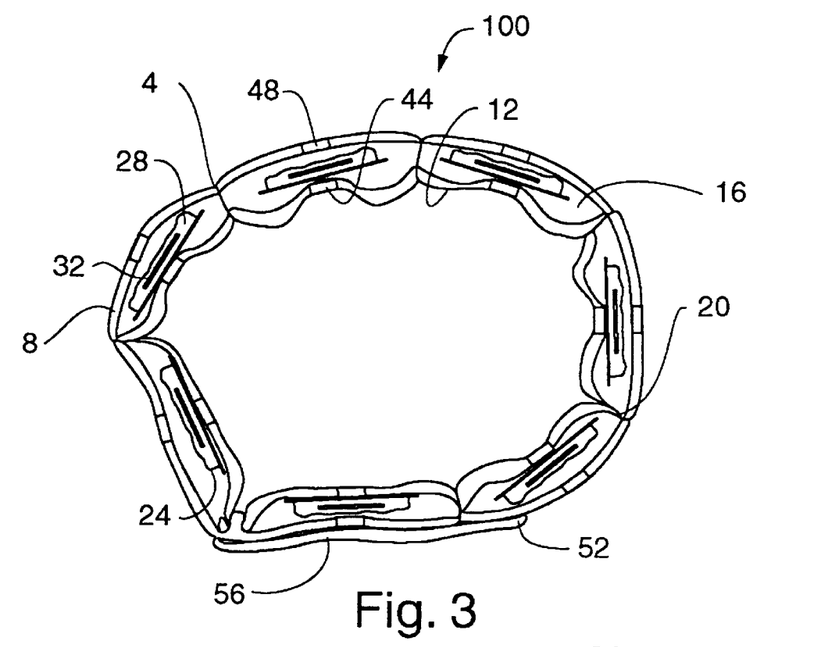
FIG. 3 is a cross-sectional view of one embodiment of the present invention showing a plurality of packets formed in a substantially circular configuration.

Referring now to FIGS. 1 and 2, an apparatus for simultaneously applying magnetic and cold therapy is generally identified by reference numeral 100. As shown, the apparatus 100 generally comprises a no pil sheath 4 having an exterior 8 made from a suitable material, such as from Neoprene or Tricot fabric, and an interior 12 made from, for example, terry cloth or lightweight, cold conductive mesh fabric. Pockets 16, also illustrated in FIG. 3, between the exterior Neoprene or Tricot fabric 8 and the interior terry cloth or cold conductive fabric 12 are formed by sew lines 20 (or by mated plastic material), such that each pocket is capable of containing a magnetic gel packet 24.

Figure 4A:
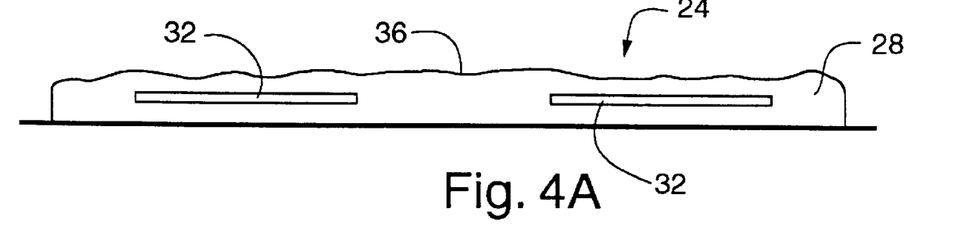
FIG. 4A is a cross-sectional view of a gel packet in accordance with an embodiment of the present invention having a magnetic element transversely positioned therein.
Figure 4B:
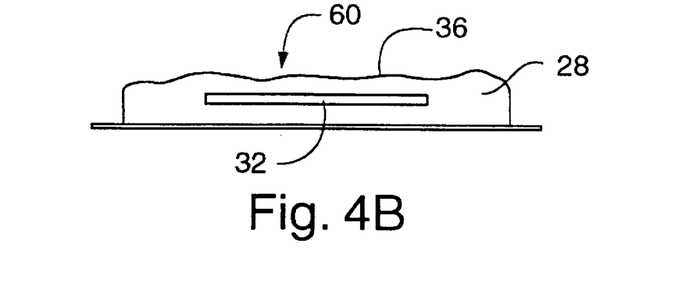
FIG. 4B is a cross-sectional view of a gel packet in accordance with another embodiment of the present invention.
Figure 5:
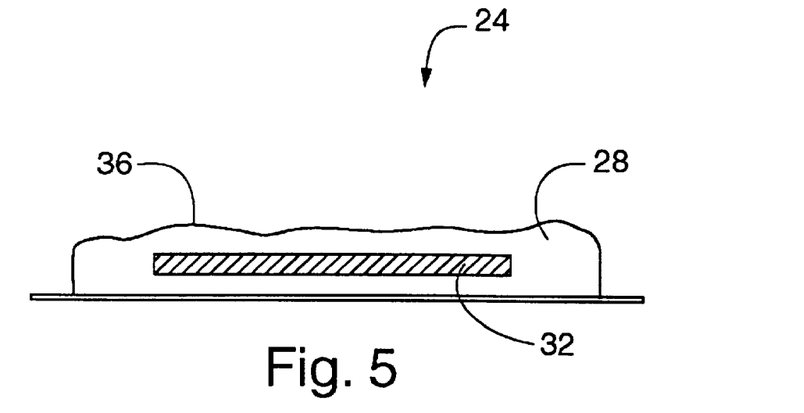
FIG. 5 is an end on cross-sectional view of a gel packet in accordance with a further embodiment of the present invention.
Figure 6:
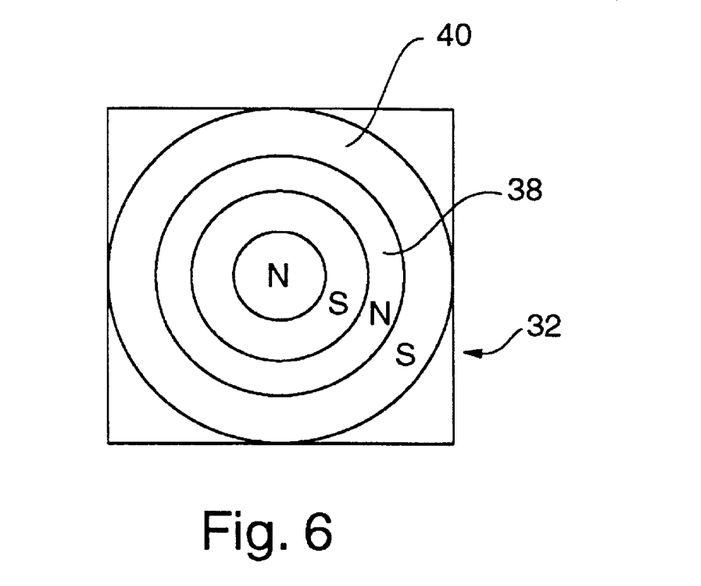
FIG. 6 is a plan view of a magnetic element in accordance with an embodiment of the present invention.

Referring now to FIGS. 4A, 4B and 5, each magnetic gel packet 24, contains a gel 28, for instance glycol and water, and at least one flexible or non-flexible magnet 32, within a membrane or sheath 36. In one embodiment, the sheath is impermeable to water. According to a preferred embodiment, each magnet 32, as shown in FIG. 6, consists of alternating north 38 and south 40 poles spaced about 4 mm to about 6 mm apart in a concentric pattern. In an alternative embodiment, illustrated in FIG. 10, the magnets 32 are generally rectangular in shape, and have alternating north 38 and south 40 polarity. The north 38 and south 40 poles in this second embodiment may be spaced about 4 mm to about 6 mm apart. The spacing of the poles of either magnet may be varied, however, to suit different applications. In the embodiment of the magnet 32 illustrated in FIG.

Figure 10:
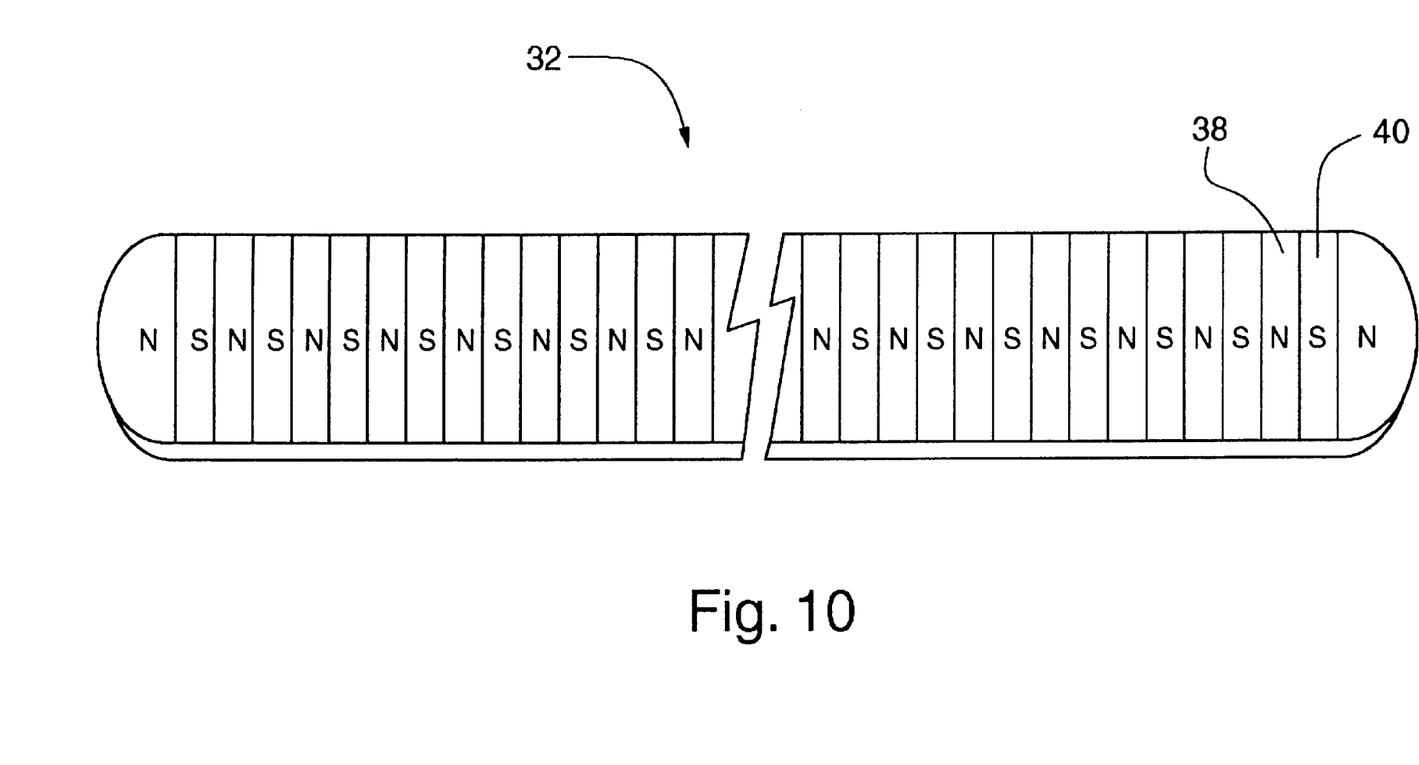
FIG. 10 is a plan view of a magnetic element in accordance with another embodiment of the present invention.

10, the magnets may be comprised of a plurality of bar magnets 8 mm to 12 mm in length.

To use the device 100, the magnetic gel packets 24 are cooled to a temperature substantially lower than that of the body part to be treated (e.g., cooled to a temperature just above freezing of the glycol, gel and water based material), and are then inserted into each of the pockets 16. The magnetic gel packets 24 can be secured in the pockets 16 by engaging the female snap receptacle 44 with the male snap portion 48 (or alternatively secured by hook and loop structures such as Velcro™). Once the magnetic gel packets 24 have been placed inside the pockets 16, the device 100 is ready to be wrapped around or placed on the body part to be treated. The entire apparatus is secured to the human body or animal part by hook and loop closures (FIGS. 1 and 7). The loop portion of the hook and loop closure may be a separate strip of loop material, or the exterior 8 of the device 100 itself. The hook 52 material may be provided on a tab or strap 56 (FIGS. 1 and 3) attached to the sheath 4. As an alternative to cooling the magnetic gel packets 24 separately, the device may be cooled as a single unit and then placed on the human or animal body part.

In one embodiment, the invention is 22 inches in length and 10 inches in width and has incorporated a universal sizing design that can wrap around a body part that is from 3.0" to 6.5" in diameter. However, by adjoining more than one unit in tandem with another, based on the preferred size and on the actual weight of the user, larger sizes can be accommodated and are within the scope of the present invention. According to one embodiment, one end of the sheath 4 (FIG. 3) includes seven pairs of female 44 and male 48 snaps for easy insertion and removal of seven cylindrical magnetic gel packets 24. In particular, for a sheath 4 (FIG. 1) that is 10 inches in length, each magnetic gel packet 24 is 9.5" in length and approximately 2.25" in width. According to another embodiment 200 (FIG. 7) there are five pairs of female 44 and male 48 snaps for easy insertion and removal of five magnetic gel packets 24 and 60. For an embodiment with a sheath 4 (FIG. 7) that includes two different pocket 16 sizes, one at 10 inches in length and one at 5.5 inches in length, the magnetic gel packet 24 (FIG. 4A) is 9.5" in length and approximately 2.25" in width and the magnetic gel packet 60 (FIG. 4B) is 5.0" in length and approximately 2.25" in width. Note that embodiments of these devices 100 and 200 having these dimensions are particularly useful for treating foot, ankle, shin, knee, thigh, leg, hand, wrist, forearm, elbow, back, hip, buttocks, shoulder and neck injuries.

Additionally, each magnetic gel packet 24 and 60 includes an effective amount of glycol and gel 28 in combination with water to sufficiently distribute magnetic flux through each packet 24 and 60. In one embodiment of magnetic gel packet 24, 11.0 ounces of nontoxic, medical grade, cold therapy gel 28 is used. The cold therapy gel may consist of substances such as water to which glycerol or some other agent to prevent freezing has been added, with or without a thickening agent (for example a linear, non cross linked polymer); polyacrylamide gel; polyvinyl alcohol covering a support of polyurethane foam; a solution of aqueous polyvinyl alcohol; and cross linked water absorbing polymers. In addition to the cold therapy gel 28, each magnetic gel packet 24 and 60 may also include one or more flexible or non-flexible magnets 32 having a length of approximately 9.0" and 4.5" respectively, a width of approximately 1.5", and a thickness of approximately .030". In one embodiment these magnets each have a magnetic flux density of 1500 gauss. Each magnet 32 may have from approximately 4 to 6 poles wherein fifty percent of these are north poles and the remainder being south poles.

Figure 8:
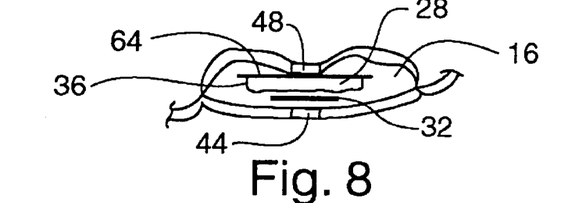
FIG. 8 is an end on view of a sheath pocket with a separate gel packet and magnet in accordance with an embodiment of the present invention.

In a preferred embodiment, illustrated in FIG. 8, the magnets 32 are not contained within gel packets 24 and 60. In this embodiment, the magnets 32 may be held or sewn in the pockets 16 of the sheath 4, or in additional pockets (not shown). According to this embodiment, the sheath 36 of the non-magnetic gel packets 64 contains only gel 28, and does not enclose any magnets 32. The configuration illustrated in FIG. 8 allows the magnets 32 to be closer to the body, maximizing their effectiveness.

The magnets 32 also need not be flexible. For example, the magnets 32 may be composed of many small flexible or rigid magnets (e.g., each magnet being one inch in length and one-half inch in width, or sized such that they substantially fill the sheath), thus allowing the present invention to maintain its overall flexibility, and to allow for the insertion of additional magnets 32. The magnets 32 may be neodymium, rare earth, ceramic, aluminum, silver, platinum, nickel and/or cobalt type magnets, or any other type of permanent magnet. Magnetic fabrics and textiles can also be used having magnetic fibers incorporated therein. The magnets 32 and the gel packets 24 or 60 can be inserted into the pockets 16 of any sheath 4 constructed in accordance with the present invention. Indeed, it should be understood that the present invention is intended to broadly encompass the use of any magnetic field and/or a current capable of conducting a charge, in combination with cold and/or ice therapy.

Figure 9:
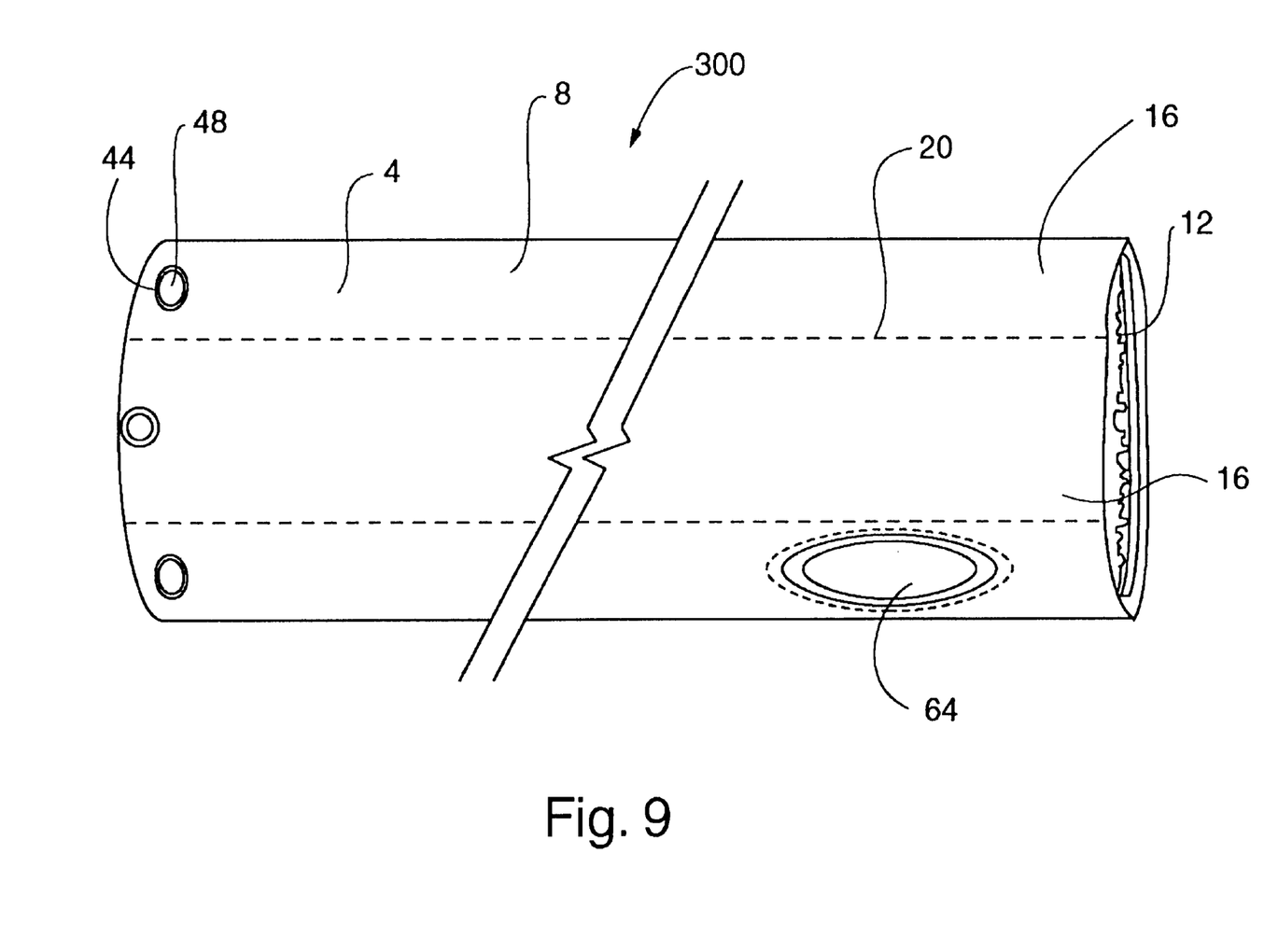
FIG. 9 is a perspective view of one embodiment of the apparatus of the present invention, featuring an aperture to accommodate a heel, digit or joint.

Referring now to FIG. 9, an additional embodiment of the invention 300 features an aperture 64 to accommodate a heel, digit or joint. This feature allows the user to obtain a closer fit when the invention is being used on a wrist or ankle. The device for providing simultaneous magnetic and cold therapy 300 is similar in construction to the other disclosed embodiments, and generally includes a no pil sheath for having an exterior 8 made from a suitably soft and flexible material. According to a preferred embodiment, the exterior 8 functions as the loop portion of a hook and loop closure for affixing the device to an appendage. The interior 12 of the sheath 4 is preferably made from a lightweight, cold conductive fabric, such as terry cloth. Pockets 16 are formed between the exterior 8 and interior 12 fabrics by sew lines 20. The pockets 16 are adapted to receive magnetic gel packets 24 and 60, or separate magnets 32 and gel packets 64. The nonmagnetic gel packets 64 and/or magnets 32, or the magnetic gel packets 24 or 60, may be secured in the pockets 16 by snaps having female 44 and male 48 portions. Alternatively, the pockets 16 may be secured by hook and loop closures. The sheath 4 may be secured about an arm or leg using a hook and loop closure (not shown).

In use, the device described herein may be cooled to a temperature substantially below that of, for example, a human body; placed on the body part to be treated; and removed from the body part after the desired time for applying the therapy, e.g. two hours. When the device is applied to a joint, such as an ankle, elbow, wrist, or knee, the device may be secured about the limb using provided closure means, such as an elastic or a hook and loop closure. As an alternative to cooling the entire device, in one embodiment the gel packets may be removed from the sheath for cooling. Then, immediately before use, the gel packets may be placed in the sheath, and the sheath attached or applied to the body part to be treated. Alternatively, the entire device, or the gel packets alone, may be heated prior to use, when heat therapy is desired. Similarly, in an embodiment that provides for separate gel packets and magnets, individual components may be either heated or cooled prior to use, and may be used separately or in combination with each other.

While various embodiments of the present invention have been described in detail, it is apparent that further modifications and adaptations of the invention will occur to those skilled in the art. However, it is to be expressly understood that such modifications and adaptations are within the spirit and scope of the present invention. It is intended that the appended claims be construed to include all alternative embodiments as permitted by the prior art.

What is claimed is:

1. A universal compression device for providing simultaneous magnetic flux and cold therapy, comprising:
   a sheath including a first layer and a second layer, and having pockets formed there between, wherein said pockets are parallel and adjacent to one another, and wherein said pockets are accessible at a first and;
   a plurality of magnets, located parallel and adjacent to said first layer of said sheath;
   a plurality of individual or multiple gel packets adapted to be inserted in said pockets; and
   a plurality of closures for securing said gel packets on or in said pockets.

2. The device of claim 1, wherein the plurality of closure comprise a band affixed to said second layer of said sheath for securing said device to a body part and producing compression.

3. The device of claim 1, wherein at least one of said plurality of magnets is located within or attached to said plurality of gel packets.

4. The device of claim 1, wherein said plurality of magnets each have a north pole and a south pole that are axial, linear, concentric, unipolar or multipolar to each other.

5. The device of claim 1, wherein said plurality of magnets each have a north pole that is adjacent or concurrent to a south pole.

6. The device of claim 1, wherein said plurality of magnets are affixed to or included within said sheath.

7. The device of claim 1, wherein said magnets are flexible or rigid.

8. The device of claim 1, wherein each of said plurality of flexible or rigid magnets has a magnetic flux density of from about 100 gauss to about 5000 gauss.

9. The device of claim 1, wherein said gel is a glycol liquid gel.

10. The device of claim 1, wherein said plurality of magnets are removable from said sheath.

11. A method for simultaneously applying compression, magnetic flux and cold therapy, comprising:
    cooling one or more flexible packets having a liquid gel therein; and
    applying a flexible sheath to which said packets and one or more magnets are affixed to an injured tissue area, wherein compression, cold and magnetic flux are simultaneously applied to the injured tissue area.

12. A method as claimed in claim 11, wherein said step of cooling includes cooling said packets to less than 32 degrees Fahrenheit with said gel remaining flexible and pliable.

13. A method as claimed in claim 11, wherein said step of applying includes wrapping said sheaths about an extremity of animal or human body tissue.

* * * * *